United States Patent [19]

Crutchfield

[11] 4,419,258

[45] Dec. 6, 1983

[54] DIALKYL GLYOXYLATE SURFACTANTS

[75] Inventor: Marvin M. Crutchfield, Creve Coeur, Mo.

[73] Assignee: Monsanto Company, St. Louis, Mo.

[21] Appl. No.: 430,551

[22] Filed: Sep. 30, 1982

[51] Int. Cl.$^3$ .......................... C07C 59/10; C11D 1/04
[52] U.S. Cl. .............................. 252/89.1; 252/174.21; 252/174.24; 260/501.13; 260/501.17; 562/587
[58] Field of Search ...................... 252/174.21, 174.24, 252/89.1; 562/587; 260/501.13, 501.17

[56] References Cited

U.S. PATENT DOCUMENTS

| | | | |
|---|---|---|---|
| 3,896,040 | 7/1975 | Danesh | 252/174.21 |
| 3,941,710 | 3/1976 | Gilbert et al. | 252/99 |
| 4,098,818 | 7/1978 | Krummel et al. | 260/501.17 |
| 4,144,226 | 3/1979 | Crutchfield et al. | 562/587 |
| 4,146,495 | 3/1979 | Crutchfield et al. | 252/174.21 |
| 4,169,934 | 10/1979 | Papanu | 252/156 |
| 4,204,052 | 5/1980 | Crutchfield et al. | 252/174.24 |

Primary Examiner—John E. Kittle
Assistant Examiner—Mukund J. Shah
Attorney, Agent, or Firm—A. H. Cole; A. E. Hoffman; R. C. Griesbauer

[57] ABSTRACT

Dialkyl glyoxylates useful as anionic surfactants are disclosed. The dialkyl glyoxylates are particularly effective in removing soils from fabrics under laundering conditions. Detergent compositions containing the dialkyl glyoxylates and detergency builders are disclosed.

10 Claims, No Drawings

DIALKYL GLYOXYLATE SURFACTANTS

BACKGROUND OF THE INVENTION

Surfactants are surface-active substances having both hydrophobic and hydrophilic properties which reduce the surface tension of water and are widely used as wetting agents, emulsifiers, dispersing agents, and the like in a wide variety of products, for example, detergent formulations, cosmetics, protective coatings, adhesives, lubricants, and pharmaceuticals. New surfactants are highly desirable because surfactants having different properties are in demand for a variety of applications, including industrial and household cleaners. For example, a major problem in the field of home laundry detergent formulations is the selection of surfactants to compensate for the low wash water temperatures to conserve energy and the changing fabric mix due to the popularity of synthetic fibers such as polyester and polyester-cotton blends. Surfactants which have more soluble calcium salts than soaps are desirable for use with hard water.

One advantage of this invention is providing a class of novel compounds that are useful as anionic surfactants. Another advantage is providing a class of novel anionic surfactants which are readily biodegraded. Another advantage is detergent formulations containing one or more compounds of this invention having effective cleaning performance. These and other advantages are disclosed in more detail hereinafter.

SUMMARY OF THE INVENTION

This invention provides a class of novel surfactant compounds which are dialkyl glyoxylates. In preferred embodiments, these compounds have the formula

wherein each R and R' are independently a $C_6$–$C_{10}$ aliphatic group or said aliphatic group connected to an average in the range of about 1 to about 3 oxyethylene (—O—$CH_2CH_2$—) units and M is an alkali metal, ammonium or alkanolammonium. Also provided by the invention are effective detergent compositions comprising an effective amount of the dialkyl glyoxylate and a detergency builder.

DETAILED DESCRIPTION OF THE INVENTION

The dialkyl glyoxylates of this invention are particularly useful as detergent surfactants in formulations for laundering fabrics. While not intending to be limited by theory, it is believed that the dialkyl acetal glyoxylates of this invention demonstrate excellent surfactant properties in view of their high interfacial coverage per mole due to the large hydrophobe cross-section provided by the two tails R and R'. Thus, effective surfactants are provided from readily available starting materials.

In the general formula for the dialkyl acetal glyoxylates of this invention, R and R' can be any $C_6$–$C_{10}$ aliphatic group. For example, the aliphatic group can be straight or branched-chain alkyl or such an alkyl connected to an average in the range of from about 1 to about 3 oxyethylene (—O—$CH_2CH_2$—) units. R and R' can be the same or different aliphatic groups. R and R' can be varied by the selection of the alcohol used in the reaction scheme for making the dialkyl glyoxylates of the present invention as disclosed in further detail hereinafter. For example, $C_6$–$C_{10}$ straight or branched-chain alcohols, mixtures of such alcohols or alcohols ethoxylated with an average in the range of about 1 to about 3 oxyethylene units can be used to prepare dialkyl glyoxylates of the present invention.

Aliphatic groups free of oxyethylene units are preferred. Particularly preferred are the dialkyl glyoxylates wherein R and R' are independently a straight or branched-chain alkyl each having an average of 6 through 10 carbon atoms. More preferably each R and R' is a straight chain alkyl.

It is preferred that R and R' when taken together contain 12 to 20 carbon atoms, more preferably 14 to 18 carbon atoms.

Substituent M is alkali metal, ammonium or substituted ammonium such as alkanol ammonium, for example, mono-, di-, or triethanolammonium. Preferably M is sodium or potassium particularly sodium.

A preferred general reaction scheme for preparing the dialkyl glyoxylates of this invention is as follows:

Step 1: Preparation of the acetals

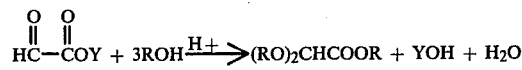

or

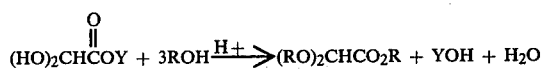

if the hydrated form of the glyoxylate starting material is used, where Y is H or lower alkyl, e.g. methyl and R is as defined above or a mixture of R and R' as defined above. Use of a refluxing solvent such as toluene to control the temperature of the reaction is useful but not essential to the reaction.

Step 2: Saponification

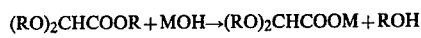

where R and M are as defined above. The ROH produced in the saponification of the ester can be recycled to step 1 if desired. The solid sodium salts can be isolated for use as pure surfactants or the crude reaction mixture containing excess ROH plus product surfactant may be preferentially used in some cases as where the presence of the excess ROH as solvent is beneficial as, for example, in some industrial cleaning operations.

In the practice of this invention on an industrial scale, a ready low cost source of the required $C_6$–$C_{10}$ alcohols are the plasticizer range alcohols such as n-octyl alcohol, 2-ethylhexyl alcohol, and isomeric mixtures of alcohols such as $C_7$ alcohols made from linear hexenes by the oxoprocess.

The preparation of the dialkyl glyoxylate is further illustrated by the following descriptions wherein all parts and percentages are by weight unless otherwise indicated.

EXAMPLE 1

Sodium dihexyl glyoxylate

In a suitable vessel fitted with a Dean and Stark condenser, a mixture of 318 g (3.1 moles) of n-hexanol, 88 g (1 mole) of freshly distilled methyl glyoxylate, 1.5 g of toluene sulfonic acid as catalyst and 500 ml of toluene solvent was refluxed. The first part of the distillate showed two layers which contain toluene, water and methanol. Approximately 200 ml of this distillate were discarded over a period of three hours before the new distillate became free of methanol and only water (lower layer) and toluene began to distill out. The reaction was allowed to continue for several hours until no more water was obtained. The mixture was allowed to cool to room temperature and 42 g (1.05 moles) of sodium hydroxide in 300 ml of 50% ethanol were added slowly with stirring. The mixture was then refluxed for two hours after which time it was concentrated to a viscous liquid on a rotary evaporator. The residue was then transferred to a 2-liter beaker and sufficient acetone was added to precipitate the product completely. The mixture was allowed to settle and the clear acetone solution was decanted. The rest was filtered with suction and then dissolved in warm isopropyl alcohol. This solution was cooled to about 5° C., filtered to remove a small amount of by-product, and then the solution was evaporated to dryness in a rotary evaporator to provide a white solid which was washed with acetone and dried in an evacuated desiccator. Yield of sodium dihexyl glyoxylate was 83% by weight assaying 4.6% $H_2O$.

| Analysis: | % | Found | Calculated 4.6% $H_2O$ |
|---|---|---|---|
| | C | 56.98 | 56.94 |
| | H | 9.51 | 9.70 |

EXAMPLE 2

Sodium diheptyl glyoxylate

Using the procedure of Example 1, 262 g (2.26 moles) of an isomeric mixture of $C_7$ alcohols containing approximately 57% n-heptanol, 30% 2-methyl hexanol, and 12% 2-ethyl pentanol, prepared by the oxo-process from linear hexenes, was reacted with 65 g (0.75 mole) methyl glyoxylate in the presence of 2.0 g (0.012 mole) toluene sulfonic acid in 500 ml of toluene. Heating to maintain reflux was continued overnight until no more water appeared in the distillate. The reaction mixture was cooled and 32 g (0.8 mole) sodium hydroxide was added and the mixture was refluxed. Following clean up as in Example 1 sodium diheptyl glyoxylate, $(C_7H_{15}O)_2CHCO_2Na$ as an off-white solid, was obtained.

It exhibited a critical micelle concentration in distilled water of 0.26% and a limiting surface tension value of 30 dyne/cm at higher concentrations.

| Analysis: | % | Found | Calculated 4.10% $H_2O$ |
|---|---|---|---|
| | C | 59.38 | 59.38 |
| | H | 10.83 | 10.11 |

EXAMPLE 3

Sodium dioctyl glyoxylate

Following the procedure of Example 1, sodium dioctyl glyoxylate was prepared from 88 g (1 mole) freshly distilled methyl glyoxylate 403 g (3.1 moles) n-octyl alcohol, 3 g (0.018 mole) toluene sulfonic acid, and saponified with 42 g (1.05 moles) sodium hydroxide. Yield was 285 g or 83% of theory assaying 5.9% $H_2O$.

| Analysis: | % | Found | Calculated 5.9% $H_2O$ |
|---|---|---|---|
| | C | 60.10 | 60.10 |
| | H | 10.61 | 10.46 |

The critical micelle concentration in distilled water was 0.1% by weight and the limiting surface tension was 25 dyne/cm.

EXAMPLE 4

Sodium dinonyl glyoxylate

A mixture of 18.42 g (0.20 mole) of glyoxylic acid, 90.00 g (0.62 mole) of 1-nonanol, 0.32 g (0.0017 mole) of p-toluene sulfonic acid, and 150 ml of toluene were refluxed using a Dean-Stark trap. The distillate showed two layers; water and toluene. The reaction was allowed to continue refluxing for several hours until no more water was collected. The mixture was cooled to room temperature and 16.90 g (0.42 mole) of NaOH in 120 ml of 50% ethanol was added slowly with stirring. After addition was complete, the mixture was refluxed for 2 hours and concentrated on a rotary evaporator. The crude product was precipitated with acetone and partially dried by suction filtration. It was then dissolved in warm isopropanol, cooled, and filtered to remove a small amount of an unidentified by-product. The filtrate was reheated and treated with decolorizing carbon. The isopropanol was removed by rotary evaporation and the product was once again precipitated with acetone. The product, along with the acetone, was well mixed using a mortar and pestle chilled in dry ice. The product was isolated by suction filtration and dried in a vacuum oven (40° C.) to yield 43.19 g (59%) of light tan, waxy crystals (m.p. 297°-300° C.; critical micelle concentration 0.05%). A second prep was done with similar results.

| Analysis: | % | Found | Calculated 5.3% $H_2O$ |
|---|---|---|---|
| | C | 62.07 | 62.05 |
| | H | 11.44 | 10.72 |

EXAMPLE 5

Sodium di(2-ethyl hexyl)glyoxylate

A mixture of 74.04 g (1.00 mole) of glyoxylic acid, 457.95 g (3.50 moles) of 2-ethyl hexanol, 1.5 g (0.008 mole) of p-toluene sulfonic acid, and 500 ml of toluene were refluxed using a Dean-Stark trap. The distillate showed two layers; water and toluene. Refluxing was continued for several hours, until no further water was collected. The mixture was cooled to room temperature and 32.80 g (0.82 mole) of NaOH in 250 ml of 50% ethanol was added slowly with stirring. After addition was complete, the mixture was refluxed for 2 hours and concentrated on a rotary evaporator to yield 435.40 g of a slightly viscous liquid as the crude product containing dialkyl glyoxylate surfactant and excess 2-ethyl hexanol. The product foams readily on addition to water, producing milky emulsions with cleaning properties.

EXAMPLE 6

Sodium glyoxylate acetals of CH$_3$(CH$_2$)$_5$CH$_2$OCH$_2$CH$_2$OH

A mixture of 8.82 g (0.09 mole) of glyoxylic acid, 44.20 g (0.28 mole) of CH$_3$(CH$_2$)$_5$CH$_2$OCH$_2$CHOH, 0.15 g (0.00077 mole) of p-toluene sulfonic acid and 110 ml of toluene were refluxed using a Dean-Stark trap. The distillate showed two layers; water and toluene. The reaction was allowed to reflux for several hours until no more water was collected. (Only 75% theoretical amount of water was collected). The mixture was cooled to room temperature and 3.74 g (0.09 mole) of NaOH in 80 ml of 50% ethanol was added slowly with stirring. After addition was complete, the mixture was heated to reflux for 2 hours. After cooling, a small amount of white ppt settled out of the solution. The precipitate was removed by filtration and a portion of the filtrate was concentrated on a rotary evaporator to yield a viscous liquid as the crude product. Acetone and isopropanol addition failed to ppt a solid product. Upon addition of H$_2$O a gel formed. In dilute solutions of distilled water the product showed good foaming properties.

Representative dialkyl glyoxylates of this invention were tested for surfactant properties. The critical micelle concentration (CMC) at 25° C. in distilled water was 1.3% for sodium dihexyl glyoxylate, 0.26% for sodium di-heptyl (isomeric mixture) glyoxylate, 0.095% for sodium di-octyl glyoxylate, and 0.05% for sodium dinonylglyoxylate. Limiting surface tensions were 25-30 dynes/cm for all. This compares favorably with the prominent detergent surfactant linear C$_{10}$-C$_{15}$ alkylbenzene sulfonate (LAS) having a CMC of 0.11% and limiting surface tension of about 35 dynes/cm.

The dialkyl glyoxylates behave similar to normal soaps of the same carbon number in many functionally useful properties, for example, lather formation, foaming, cleaning, emulsification, and wetting. They are far superior to soaps in their ability to resist precipitation of insoluble Ca++ salts in hard water. The dialkyl glyoxylates, while quite stable in basic solution, hydrolyze readily in neutral to acidic solution to provide a desirably rapid chemical pathway to non-reversible loss of surfactant properties and break down into smaller naturally biodegradable components.

As described above, the dialkyl glyoxylates of the present invention are particularly useful as detergent surfactants. The detergent compositions of the present invention may be in the form of solids, for example, granules or powders, semi-solid pastes or gels, or liquids containing from about 0.005% to about 99%, preferably from about 3% to about 50%, more preferably from about 5% to about 25% by weight of the dialkyl glyoxylate.

The detergent compositions can contain one or more organic co-surfactants selected from the group consisting of nonionic, anionic, cationic, ampholytic, and zwitterionic surfactants or mixtures thereof.

Specific preferred anionic co-surfactants include the linear C$_9$-C$_{15}$ alkylbenzene sulfonates (LAS); the branched C$_9$-C$_{15}$ alkylbenzene sulfonates (ABS); the tallow alkyl sulfates; the coconut alkyl glyceryl ether sulfonates; the mixtures of higher fatty acid soaps containing from 10 to 18 carbon atoms; and the sulfated condensation products of mixed C$_{10}$-C$_{18}$ fatty alcohols with from about 1 to about 14 moles of ethylene oxide. The weight ratio of the dialkyl glyoxylates to the anionic co-surfactant is from about 1:3 to about 3:1, preferably from about 1:1 to about 2:1.

Examples of suitable nonionic co-surfactants include alkylene oxide condensates of mono and polyhydroxy alcohols, alkyl phenols, fatty acid amides and fatty amines; amine oxides; sugar derivatives such as sucrose monopalmitate; long chain tertiary phosphine oxides; dialkyl sulfoxides; fatty acid amides and the like.

Examples of suitable zwitterionic co-surfactants include derivatives of aliphatic quaternary ammonium compounds such as 3-(N,N-dimethyl-N-hexadecylammonia)propane-1-sulfonate and its 2-hydroxy propane analog. Examples of suitable amphoteric co-surfactants include betaines, sulfobetaines and fatty acid imidazole carboxylates and sulfonates.

The detergent compositions of this invention preferably also contain from about 1% to about 95%, more preferably from about 5% to about 75%, by weight of detergent builder materials. Detergency builders are generally characterized by an ability to sequester most of the calcium and/or magnesium ions in the wash water since these ions are generally detrimental to the detergency process. Builder materials may also be used to maintain or assist in maintaining an alkaline pH in a washing solution.

Detergency builders commonly taught for use in detergent compositions are suitable for use in the detergent compositions of this invention. Useful builders include any of the conventional inorganic and organic water-soluble builder salts. For example, such builders can be water-soluble salts of phosphates, pyrophosphates, orthophosphates, polyphosphates, phosphonates, carbonates, silicates, carboxylates, polycarboxylates, polyacetates, and succinates.

Preferred inorganic phosphate builders include the sodium and potassium tripolyphosphates, phosphates, and hexametaphosphates. Sodium tripolyphosphate (STP) is particularly preferred. The polyphosphonates specifically include, for example, the sodium and potassium salts of ethane 1-hydroxy-1, 1-diphosphonic acid and ethane-1, 1,2-triphosphonic acid.

Non-phosphorus containing builders useful in the detergent compositions of this invention include the alkali metal, ammonium and substituted ammonium polyacetates, carboxylates, polycarboxylates, silicates and the like. Specific examples of the polyacetates and polycarboxylates include sodium, potassium, lithium, ammonium, and substituted ammonium salts of ethylene diamine tetraacetic acid, nitrilotriacetic acid, oxydisuccinic acid, mellitic acid, and citric acid. Particularly preferred is sodium nitrilotriacetate (NTA).

Preferred polycarboxylate builders for use herein are the polyacetal carboxylates fully described in U.S. Pat. No. 4,144,226, issued Mar. 13, 1979 to Crutchfield, et al, and U.S. Pat. No. 4,169,934, issued Oct. 2, 1979 to Victor D. Papanu, the disclosures of which are incorporated herein by reference. Particularly preferred is the stabilized acetal carboxylate polymer containing the recurring structure,

where n averages 50 to 200. This builder is particularly preferred since both the builder and surfactant are particularly well matched to achieve good cleaning results.

Insoluble amorphous and crystalline aluminosilicates are detergency builders useful in the present invention. Particularly useful aluminosilicates are those commonly known zeolites A, X, and P(B).

Alkali metal silicate builder materials can be used in the detergent compositions herein to enhance particulate soil removal from laundered fabrics, to provide corrosion inhibition protection to the metal parts of washing machines, and to provide pourability and avoid lumping of the detergent granules. Usually the alkali metal silicates represent about 2% to 10% by weight of the detergent composition.

Other ingredients which are conventionally used in detergent compositions can be included in the detergent compositions of the present invention. These ingredients include bleaching agents and bleach activators, soil suspending agents, soil release agents, coloring agents, suds boosters or suds suppressors, anti-tarnish agents, optical brighteners, germicides, pH adjusting agents, non-builder alkalinity sources, hydrotropes, solvents, enzymes, perfumes, fillers, colorants and the like.

The sodium dialkyl glyoxylate products of this invention are also useful in bar form, either alone or in combination with other conventional bar soap ingredients.

The sodium dialkyl glyoxylate products of Examples 1, 2, and 3 were evaluated for solid fabric detergency using a Terg-O-Tometer under the following conditions: airborne particulate/sebum soil, 100% cotton and 65%/35% polyester cotton blend fabrics; water hardness-3/2 Ca/Mg at 50 ppm and 150 ppm; detergent composition concentration 0.1%, 0.15%, 0.20%. The detergent composition evaluated contained: 20% surfactant; 35% STP; 10% $Na_2CO_3$; 6% R.U. Silicate (solids); 25% $Na_2SO_4$ and 4% $H_2O$. The results are set forth below.

| SAMPLE 100% COTTON | DET. CONC. % | ΔRd. "SEBUM SOIL" 50 ppm* | 150 ppm* |
|---|---|---|---|
| Prod. Ex 1 | 0.10 | 26.5 | 17.4 |
|  | 0.15 | 27.0 | 20.5 |
|  | 0.20 | 28.2 | 24.0 |
| Prod. Ex 2 | 0.10 | 26.5 | 16.6 |
|  | 0.15 | 28.3 | 23.2 |
|  | 0.20 | 27.3 | 25.5 |
| Prod. Ex 3 | 0.10 | 29.3 | 18.4 |
|  | 0.15 | 30.3 | 22.9 |
|  | 0.20 | 29.6 | 25.0 |
| 65/35 PE/Cotton |  |  |  |
| Prod. Ex 1 | 0.10 | 6.5 | 0.0 |
|  | 0.15 | 8.4 | 1.1 |
|  | 0.20 | 11.0 | 5.5 |
| Prod. Ex 2 | 0.10 | 7.2 | 0.0 |
|  | 0.15 | 10.0 | 2.6 |
|  | 0.20 | 11.9 | 6.0 |
| Prod. Ex 3 | 0.10 | 12.6 | 0.0 |
|  | 0.15 | 27.5 | 4.9 |
|  | 0.20 | 27.3 | 13.1 |

*Water hardness, 3/2 Ca:Mg

Using the above procedure but replacing the STP builder with a like amount of a stabilized acetal carboxylate polymer of the formula $$\begin{array}{c} +CHO+_n \\ | \\ COONa \end{array}$$

where n averages about 50 to 200 detergent compositions containing sodium dioctyl glyoxylate, linear $C_{10}$–$C_{15}$ alkyl benzene sulfonate and 50/50 mixtures thereof were evaluated. At a detergent concentration level of 0.20% essentially the same Δ Rd (29.9–30.9) was obtained for 100% cotton fabric at both hardness levels for the LAS, the sodium dioctyl glyoxylate and the 50/50 mixture of the LAS/sodium dioctyl glyoxylate. For the 65/35 PE/Cotton blend essentially the same Δ Rd (22.4–25.3) was obtained at the 50 ppm hardness level and at 150 ppm hardness. The 50/50 mixture of LAS/sodium dioctyl glyoxylate improved the results over that obtained for the sodium dioctyl glyoxylate from 14.4 to 21.3.

Although the invention has been described in terms of specified embodiments which are set forth in considerable detail, it should be understood that this is by way of illustration only and that this invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A compound of the formula:

$$\begin{array}{c} ROCHOR' \\ | \\ COOM \end{array}$$

wherein R and R' are independently a $C_6$–$C_{10}$ aliphatic group or said aliphatic group containing an average in the range of about 1 to about 3 oxyethylene units and M is alkali metal, ammonium or alkanolammonium.

2. The compound of claim 1 wherein R and R' are independently a straight or branched-chain alkyl having an average of 6 through 10 carbon atoms.

3. The compound of claim 2 wherein M is sodium or potassium.

4. The compound of claim 2 wherein R and R' when taken together contain 12 to 20 carbon atoms.

5. The compound of claim 3 wherein R and R' are the same and are n-octyl, n-nonyl or 2-ethyl hexyl.

6. The compound of claim 3 wherein R and R' are each a $C_7$ alkyl derived from an isomeric mixture of $C_7$ alcohols.

7. A detergent composition comprising a detergency builder and at least one compound of the formula:

$$\begin{array}{c} ROCHOR' \\ | \\ COOM \end{array}$$

wherein R and R' are independently a $C_6$–$C_{10}$ aliphatic group or said aliphatic group containing an average in the range of about 1 to about 3 oxyethylene units and M is alkali metal, ammonium or alkanolammonium.

8. The detergent composition of claim 7 wherein R and R' are independently a straight or branched-chain alkyl of an average of 6 through 10 carbon atoms and M is sodium or potassium.

9. The detergent composition of claim 8 also containing one or more co-surfactants selected from nonionic, anionic, zwitterionic and cationic surfactants.

10. The detergent composition of claim 8 wherein the detergency builder is a stabilized acetal carboxylate polymer of the formula:

$$\begin{array}{c} +CHO+_n \\ | \\ CO_2Na \end{array}$$

wherein n averages in the range of 50 to 200.

* * * * *